United States Patent
Majeed

(10) Patent No.: US 9,126,241 B2
(45) Date of Patent: Sep. 8, 2015

(54) CLEANING APPARATUS

(76) Inventor: Ali Waqar Majeed, Sheffield (GB)

( * ) Notice: Subject to any disclaimer, the term of this patent is extended or adjusted under 35 U.S.C. 154(b) by 518 days.

(21) Appl. No.: 13/517,210

(22) PCT Filed: Nov. 19, 2010

(86) PCT No.: PCT/GB2010/051930
§ 371 (c)(1),
(2), (4) Date: Jun. 19, 2012

(87) PCT Pub. No.: WO2011/061544
PCT Pub. Date: May 26, 2011

(65) Prior Publication Data
US 2012/0285485 A1     Nov. 15, 2012

(30) Foreign Application Priority Data

Nov. 20, 2009 (GB) .................................. 0920322.5
Aug. 4, 2010 (GB) .................................. 1013133.2

(51) Int. Cl.
| | |
|---|---|
| B08B 9/02 | (2006.01) |
| B08B 9/043 | (2006.01) |
| A61B 19/00 | (2006.01) |
| A61B 1/12 | (2006.01) |
| A61M 25/00 | (2006.01) |

(52) U.S. Cl.
CPC .............. *B08B 9/0436* (2013.01); *A61B 1/122* (2013.01); *A61B 19/34* (2013.01); *A61B 1/121* (2013.01); *A61B 2019/343* (2013.01); *A61M 25/00* (2013.01); *A61M 2025/0019* (2013.01); *B08B 9/02* (2013.01)

(58) Field of Classification Search
CPC ............ B08B 9/02; A61B 1/12; A61B 1/121; A61B 1/123; A61B 1/125; A61B 1/127
USPC .................. 134/166 C, 167 C, 168 C, 169 C; 15/104.95, 104.2, 104.3, 104.33, 304, 15/315, 395, 398
See application file for complete search history.

(56) References Cited

U.S. PATENT DOCUMENTS

| | | | |
|---|---|---|---|
| 4,546,519 A | 10/1985 | Pembroke | |
| 5,251,356 A | 10/1993 | Oaki et al. | |
| 2007/0226927 A1* | 10/2007 | Suzuki et al. ................ | 15/104.2 |

FOREIGN PATENT DOCUMENTS

| | | |
|---|---|---|
| EP | 1269908 A1 | 1/2001 |
| EP | 1785147 A2 | 5/2007 |
| EP | 1844698 A2 | 10/2007 |
| EP | 1849403 A1 | 10/2007 |
| EP | 1869565 A2 | 10/2007 |
| EP | 1785147 A3 | 12/2007 |
| EP | 1869565 A3 | 1/2008 |
| EP | 1872709 A1 | 1/2008 |
| JP | 08-275918 A | 10/1996 |
| JP | 2004-208961 | * 7/2004 |
| JP | 2004208961 A | 7/2004 |

(Continued)

*Primary Examiner* — Saeed T Chaudhry
(74) *Attorney, Agent, or Firm* — patenttm.us

(57) ABSTRACT

A cleaning apparatus (10) comprises a drive arrangement (16). A discrete holding means (12) is mountable on the drive arrangement. The holding means comprises a flexible elongate cleaning member (14) and a housing (18) for housing at least a portion of the elongate cleaning member. The cleaning apparatus further includes a transmission arrangement (20) for transmitting drive from the drive arrangement to the elongate cleaning member.

20 Claims, 13 Drawing Sheets

(56) References Cited

FOREIGN PATENT DOCUMENTS

| JP | 2005-103187 | * | 4/2005 |
| JP | 2005103187 A | | 4/2005 |
| JP | 2005111073 A | | 4/2005 |
| JP | 2006034461 A | | 2/2006 |
| JP | 2007-301247 A | | 11/2007 |
| WO | 02068134 A1 | | 9/2002 |

* cited by examiner

CLEANING APPARATUS

This invention relates to cleaning apparatus. More particularly, but not exclusively, this invention relates to cleaning apparatus for cleaning medical apparatus, such as endoscopes. At least one embodiment of the invention relates to holding arrangement for use with drive arrangements of cleaning apparatus. At least one embodiment of the invention relates to drive arrangements for use with holding arrangement for cleaning apparatus.

After use of an endoscope, it is necessary to remove waste and other contaminants therefrom. The method of cleaning involves wiping the outside to remove contaminant material. In order to clean the inside channels of the endoscope, a brush mounted on an elongate flexible cable is inserted through each of the channels manually using a reciprocating motion to ensure cleaning throughout the respective channels.

According to one aspect of this invention, there is provided a cleaning apparatus comprising a flexible elongate cleaning member, a drive arrangement, for driving the elongate cleaning member, and the cleaning apparatus further includes a transmission arrangement to transmit drive from the drive arrangement to the cleaning member to drive the cleaning member lengthwise.

The cleaning apparatus may comprise a holding arrangement to hold the flexible elongate cleaning member. The holding arrangement may be discrete from the drive arrangement, and may be mountable on the drive arrangement. The holding arrangement may comprise a housing to house the flexible elongate cleaning member.

According to a further aspect of this invention, there is provided a cleaning apparatus comprising a drive arrangement, a discrete holding arrangement mountable on the drive arrangement, the holding arrangement comprising a flexible elongate cleaning member and a housing for housing at least a portion of the elongate cleaning member, and the cleaning apparatus further including a transmission arrangement for transmitting drive from the drive arrangement to the elongate cleaning member.

According to another aspect of this invention, there is provided a method of cleaning an article comprising providing a cleaning apparatus as described above, arranging the apparatus on an article to be cleaned, and operating the drive arrangement to drive the cleaning member.

The drive arrangement may include a receiving portion in which at least a part of the holding arrangement can extend. The drive arrangement may include a driver for driving the flexible elongate cleaning member.

The cleaning apparatus may comprise an endoscope cleaner.

The holding arrangement may include a mounting element upon which the flexible elongate cleaning member is mounted. The cleaning member may extend, in use, from the mounting element through the receiving portion of the drive arrangement.

The transmission arrangement may be provided in the receiving portion, whereby drive can be transmitted to the cleaning member in the receiving portion.

According to a further aspect of this invention, there is provided a holding arrangement for use in a cleaning apparatus, the holding arrangement comprising a housing for housing a flexible elongate cleaning member, and a transmission arrangement to transmit drive from the drive arrangement to the flexible elongate cleaning member.

The holding arrangement may comprise a cartridge. The holding arrangement may be removable from the drive arrangement. The drive arrangement may secure the holding arrangement thereto. The method may comprise mounting the holding arrangement on the drive arrangement.

The holding arrangement may comprise a holding element upon which the cleaning member is held. The holding element may be rotatably mounted on the housing. The holding element may comprise a reel, and the cleaning member may be wound on the reel. The holding element may be substantially cylindrical in configuration.

The holding element may be rotatable in a first direction to feed the elongate cleaning member from the holding arrangement, and in a second direction opposite to the first direction to retract the elongate cleaning member into the holding arrangement.

The holding arrangement may comprise an urging means to urge the holding element in the second direction. The urging means may comprise a spring. Alternatively, or in addition, the holding arrangement may include bearings to facilitate movement of the holding element in the first and second directions.

The holding arrangement may comprise a main portion in which the holding element is housed. The holding arrangement may include a neck portion, which may extend forwardly of the main portion. The neck portion may comprise a tubular member.

In a further embodiment, the holding arrangement may comprise friction reducing means to reduce friction between the elongate cleaning member and the main portion during retraction of the elongate cleaning member. The friction reducing means may comprise a guide arrangement to guide the elongate cleaning member onto the holding element during retraction thereof.

In one embodiment, the guide arrangement may comprise a plurality of roller members arranged between the holding element and the main portion. In another embodiment, the friction reducing means may comprise a low friction material arranged between the holding element and the main portion. In this embodiment, the low friction material may comprise a strip of the low friction material. The low friction material may comprise PTFE.

The cleaning apparatus may comprise a gear arrangement. In one embodiment, the gear arrangement may be provided at the neck portion. Conveniently, the gear arrangement is provided in the neck portion, and may be part of the holding arrangement.

In another embodiment, the drive arrangement may comprise the gear arrangement.

The transmission arrangement may comprise at least one roller drive member for engaging the cleaning member. The transmission arrangement may comprise a plurality of roller drive members for engaging the cleaning member.

The transmission arrangement may comprise at least one pair of roller drive members. In one embodiment, the transmission arrangement may comprise two or more pairs of roller drive members. In another embodiment, the transmission arrangement may comprise one pair of roller drive members.

A feed path may be defined by the roller drive members, through which the cleaning member can extend. The roller drive members may be positioned to engage the cleaning member in the feed path.

Conveniently, the transmission arrangement includes at least a pair of opposed roller drive members. In one embodiment, the transmission arrangement may include two pairs of opposed roller drive members arranged in succession, and the path may be defined between the rollers of the, or each, pair.

In one embodiment, the gear arrangement may include gear members to transmit drive from the drive arrangement to the roller drive members and, thereby, to the cleaning member. The gear members may comprise a main gear wheel to engage the drive arrangement, and a respective further gear wheel for each roller drive member, each further gear wheel being driven by the main gear wheel either directly or indirectly.

In one embodiment, the neck portion may define a receiving aperture to receive a drive member of a driver. The main gear wheel may define a cooperating drive aperture into which the drive member can be inserted. The drive member may have co-operating formations, such as grooves to cooperate with corresponding formations, such as splines, on the drive member. The receiving aperture and the drive aperture may be aligned with each other.

In another embodiment, the gear arrangement may comprise a first gear member mounted on the driver. The gear arrangement may include a second gear member, which may be in co-operative engagement with the first gear member.

The first gear member may be in driving engagement with the second gear member. The second gear member may be driven by the first gear member when the driver is operated. The first gear member may comprise a first gear wheel. The second gear member may comprise a second gear wheel.

Each of the first and second gear members may be connected to a respective propelling member. The transmission arrangement may comprise propelled members arranged to co-operate with the propelling members on operation of the driver.

Each propelling member may comprise a receiving member for receiving a respective one of the propelled members. Each propelling member may define a polygonal recess, and each propelled member may have a corresponding polygonal configuration.

Each propelling member may define a hexagonal recess, and each propelled member may have a corresponding hexagonal configuration.

The holding arrangement may include a locating portion for locating the holding arrangement at an appropriate position on the article to be cleaned. The locating portion may be configured for directing the cleaning member into an appropriate region of the article to be cleaned.

The locating portion may define a directing conduit, which may extend through the locating portion. The cleaning member may pass through the directing conduit, in use. The locating portion may comprise an inwardly tapered forward end.

The cleaning member may protrude from the holding arrangement prior to use. Desirably, the cleaning member protrudes from the locating portion. The method may comprise manually directing the cleaning member into a desired region of the article to be cleaned, prior to operating the driver.

A fluid supply conduit may be defined on the locating portion to supply cleaning fluid, such as water, to the cleaning member to facilitate cleaning of the article. The fluid supply conduit may be in fluid communication with the directing conduit. The locating portion may be provided forwardly of the neck portion.

Impelling means may be provided to impel the holding element in the second direction. The impelling means may comprise a linkage, which may extend from the transmission arrangement to the holding element. Alternatively, the impelling means may comprise a second driver configured to drive the holding element in the second direction. The second driver may comprise a motor, such as an electric motor. The impelling means may include a linkage extending from the second driver to the holding element. The linkage may comprise a transmission rod and a gear to co-operatively engage the holding element.

According to another aspect of this invention, there is provided a drive arrangement for use with a holding arrangement for an elongate flexible cleaning member, the drive arrangement comprising a receiving portion on which the holding arrangement can be mounted, and a driver on the receiving portion for co-operative association with the holding arrangement to effect lengthwise movement of the cleaning member.

The receiving portion may define a channel through which a part of the holding arrangement can extend. The receiving portion may be tubular, and may receive a neck portion of the holding arrangement.

In one embodiment, the receiving portion may comprise a main part and a door member on the main part. The door member is configured to be opened to allow the holding arrangement to be inserted into the receiving portion. The receiving portion may comprise at least one hinge to pivotally mount the door member on the main part.

In another embodiment, the receiving portion may comprise a pair of opposed side wall members, and the neck portion of the holding arrangement may be received between the wall members.

In one embodiment, the driver may be provided in the receiving portion and may comprise a motor, such as an electric motor, and a controller for controlling the electric motor. The controller may be configured to effect selective motion of the driver, to selectively drive the cleaning member in a first lengthwise direction, second opposite lengthwise direction, or reciprocally in the first and second directions.

The driver may include a drive member for cooperative engagement with a gear arrangement of the holding arrangement. The drive member may comprise a shaft.

The drive member may be configured to be received in the part of the holding arrangement in the receiving portion. The holding arrangement may include a main gear wheel, and the drive member may drivingly engage the main gear wheel.

The drive arrangement may have a handle to facilitate the drive arrangement being held by a user. The handle may include control members associated with a processor to effect the desired operation of the driver. The control members may be in the form of buttons. The apparatus may include a power source to provide electrical power to the drive arrangement. The power source may provide electrical power to the processor.

In another embodiment, the driver may be mounted in the handle. In this embodiment, the processor may be separate from the drive arrangement. The power source may be separate from the drive arrangement. A power transmission means may be provided to transmit power to the drive arrangement. The power transmission means may comprise a cable.

According to another aspect of this invention, there is provided a cleaning member comprising a flexible elongate shaft and a plurality of brush portions at one end region of the shaft, the brush portions being spaced from each other.

The cleaning member may have two or three brush portions at said one end region of the shaft. The brush portions may be spaced from each other along the flexible shaft.

The shaft may have a distal end and a proximal end, and the cleaning member may comprise a first brush portion adjacent the distal end. The cleaning member may have a second brush portion spaced from the first brush portion in a direction towards the proximal end. The cleaning member may have a third brush portion spaced from the second brush portion in a direction towards the proximal end. The brush portions may be integral with the shaft.

The cleaning member may have a stop element on the shaft. The stop element may be arranged adjacent the further brush portion towards the proximal end relative to the further brush portion.

The stop element may be provided to prevent retraction of the cleaning member fully into the aforesaid holding arrangement.

Embodiments of the invention will now be described by way of example only, with reference to the accompanying drawings, in which.

Figure 1:
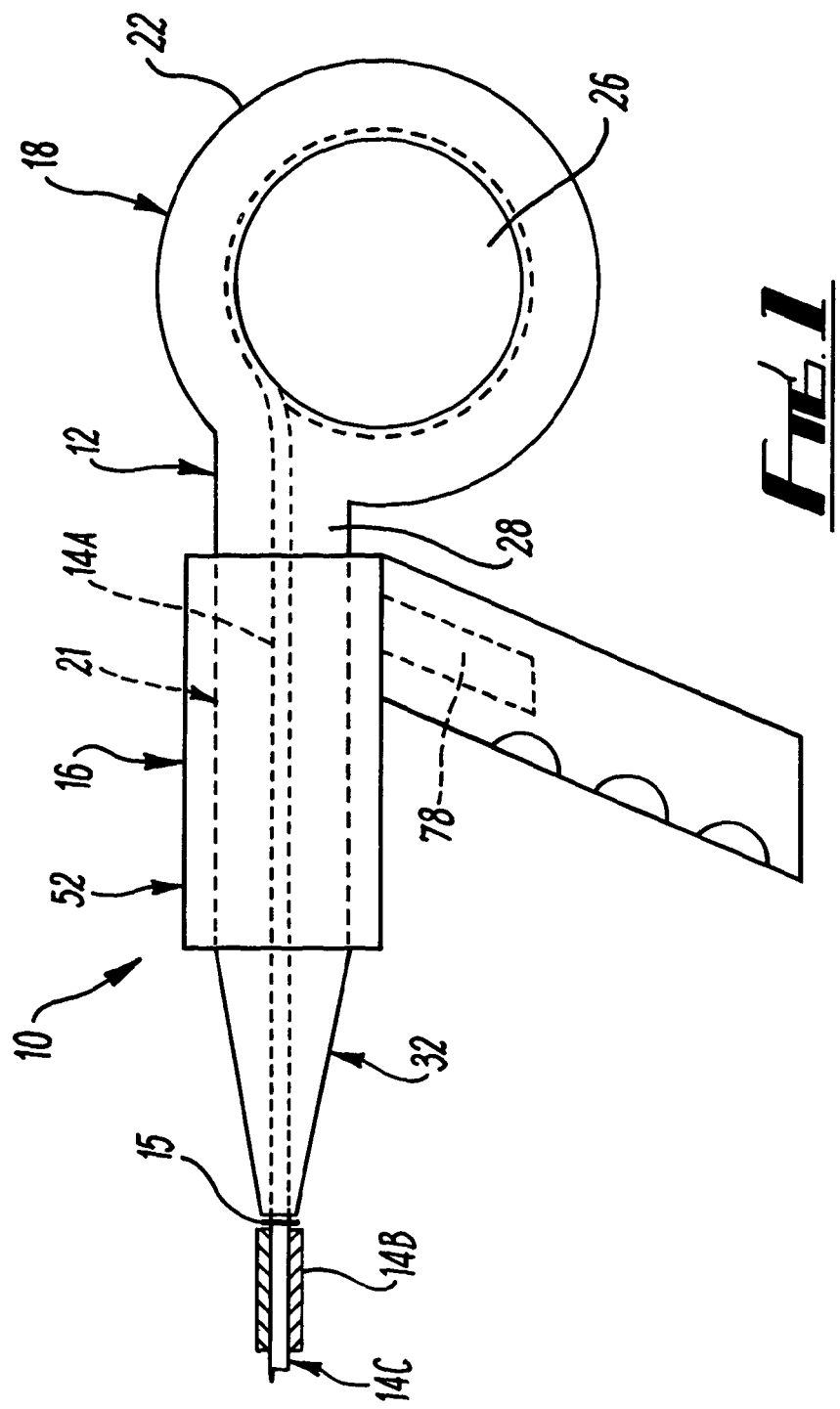
FIG. 1 is a side view of an embodiment of a cleaning apparatus.

FIG. 1 shows a cleaning apparatus 10, in the form of an endoscope cleaner. The cleaning apparatus 10 comprises a holding arrangement in the form of a cartridge 12 for holding a flexible elongate cleaning member 14 (shown in broken lines in FIG. 1), and a drive arrangement 16 on which the cartridge 12 can be mounted. As explained below, a neck portion 21 of the cartridge 12 extends through a receiving portion 52 of the drive arrangement 16. The cleaning apparatus 10 is used to clean an article, such as a medical article, for example an endoscope.

Figure 2:
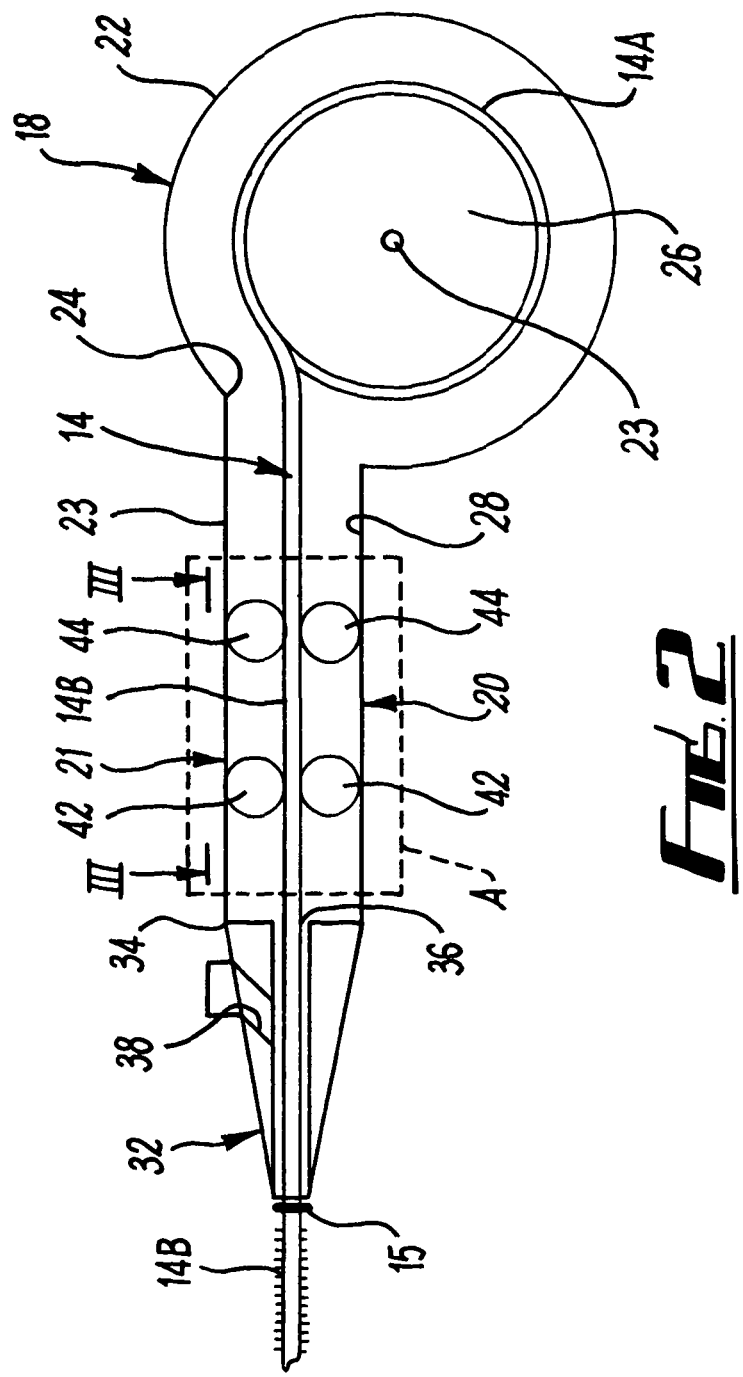
FIG. 2 is a sectional side view of a holding arrangement for use in the cleaning apparatus shown in FIG. 1.
Figure 2A:
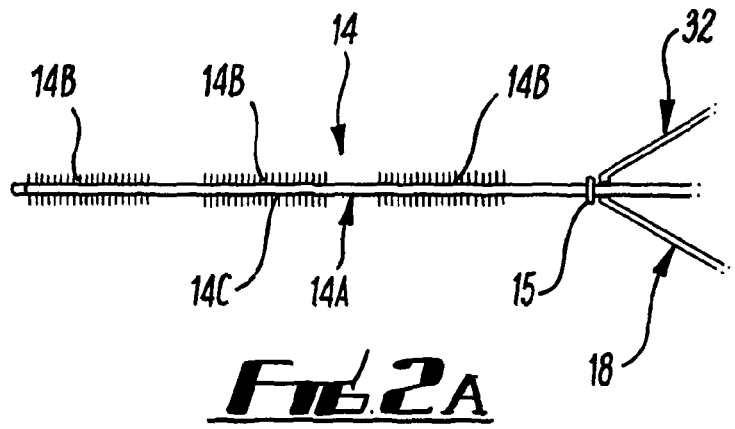
FIG. 2A shows a distal end region of a cleaning member.

Referring to FIG. 2A, an end region of the flexible elongate cleaning member 14 is shown. The elongate cleaning member 14 comprises a flexible elongate shaft 14A which is capable of being deformed to pass through channels in an endoscope. The end region of the shaft 14A is a distal end region 14C. The shaft 14A also has a proximal end region (not shown).

The elongate cleaning member 14 further includes a first, second and third brush portions 14B provided on the distal end region 14C of the shaft 14A. The three brush portions 14B are spaced from each other on the distal end region 14C of the shaft 14A.

Figure 3:
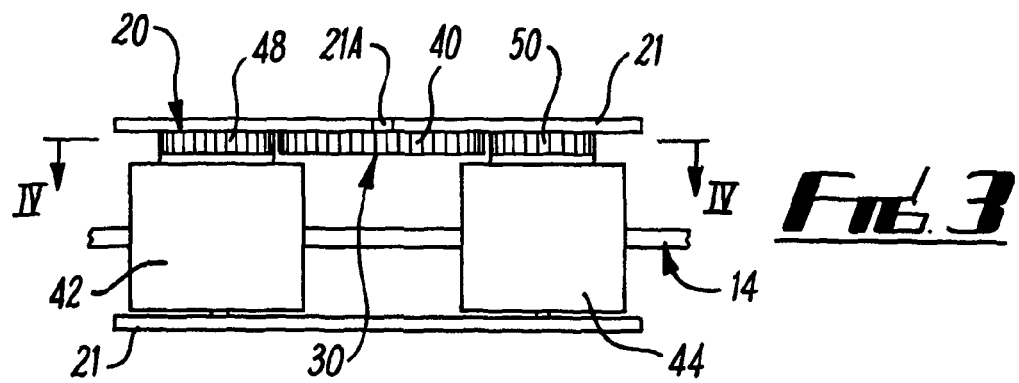
FIG. 3 is along the lines III-III of the region marked A in FIG. 2.
Figure 4:
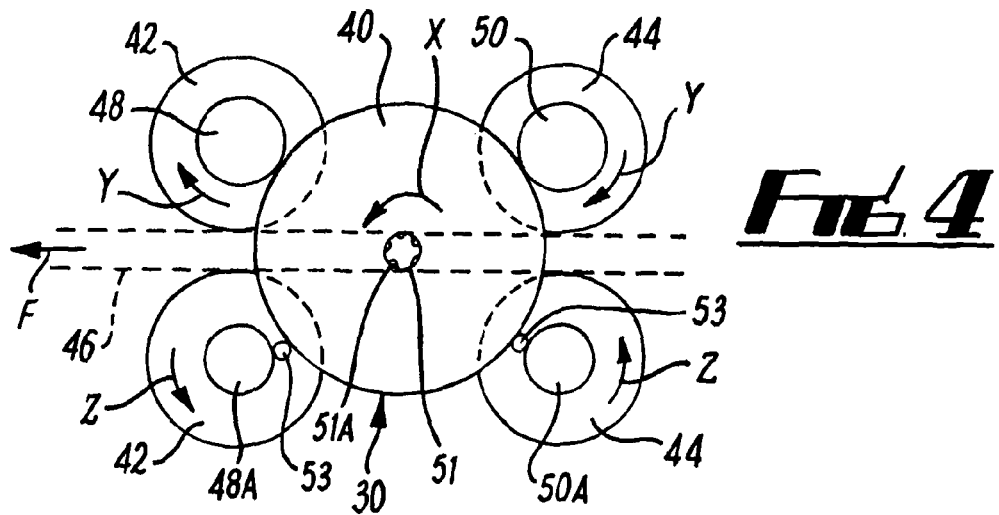
FIG. 4 is a view along the lines IV-IV in FIG. 3.

The cartridge 12 is shown in more detail in FIGS. 2, 3 and 4, and comprises a housing 18 and a transmission arrangement 20. The housing 18 comprises a mounting element 22 defining an opening 24.

The housing 18 further includes a holding element in the form of a reel 26 upon, or in, which the flexible elongate cleaning member 14 is wound. The reel 26 is rotatably mounted on the mounting element 22 at an axle 23

The housing 18 further comprises a neck portion 21 in the form of a tubular member 23 defining a channel 28 therethrough. The neck portion 21 is provided on the mounting element 22 at the opening 24.

The transmission arrangement 20 comprises a gear arrangement 30 (see FIG. 3) mounted within the channel 28 in the neck portion 21.

A locating portion 32 is mounted on the neck portion 21 at a forward end 34 of the neck portion 21. The locating portion 32 defines a conduit 36 through which the flexible elongate member 14 can pass. The locating portion 32 further defines a fluid supply conduit 38 through which cleaning fluid, for example water, can be supplied to the cleaning member 14 to facilitate cleaning of the article.

Figure 11:
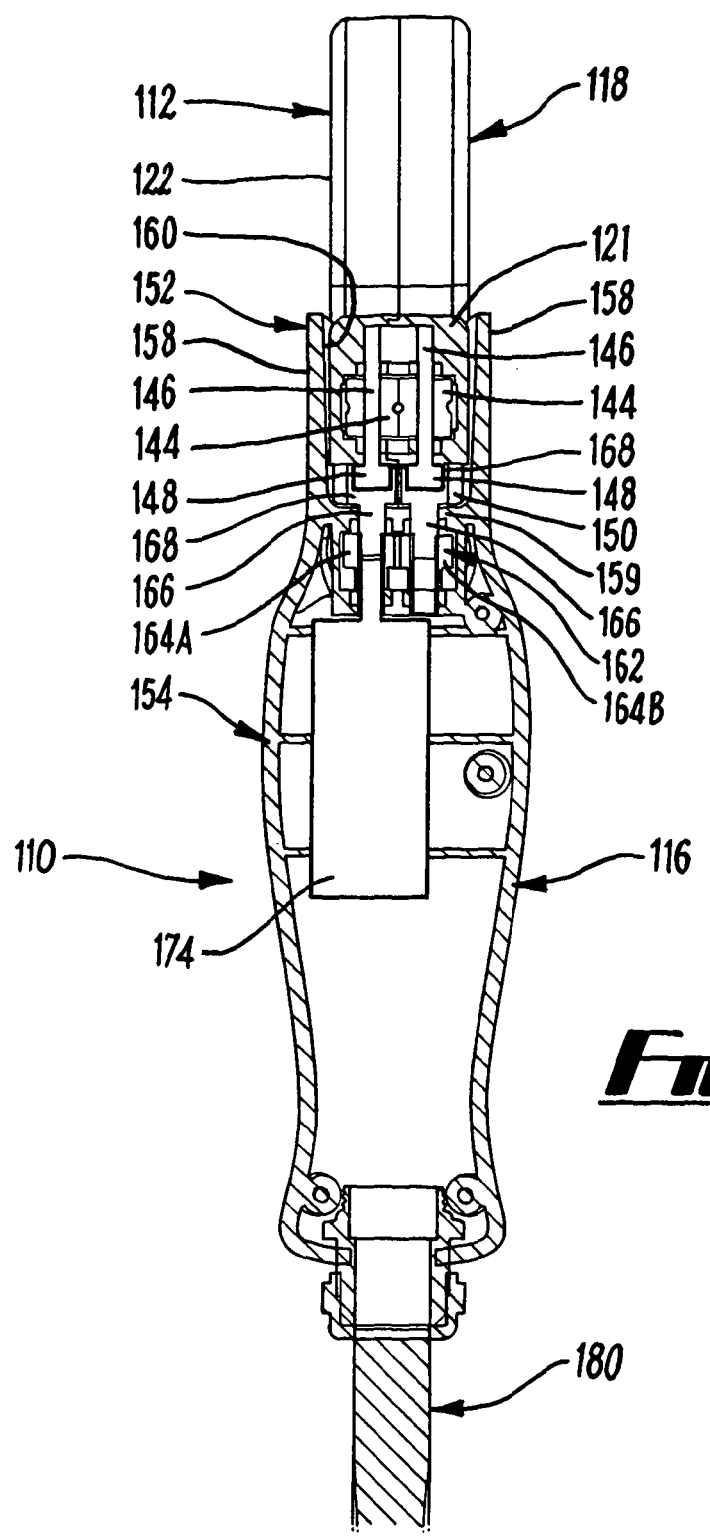
FIG. 11 shows a front sectional view of the cleaning apparatus shown in FIGS. 7 and 8.

The distal end region 14C and the three brush portions 14B of the elongate cleaning member 14 protrude from the locating portion 32, a shown in FIG. 11. A stop member 15 is provided on the shaft 14A spaced towards the proximal end region from all three brush portions 14B. The stop member 15 prevents the elongate cleaning member 14 from being fully retracted into the housing 18.

The elongate cleaning member 14 is shown in FIGS. 1 and 2, but only the brush formation 14B closest to the stop member 15 is shown. The others have been omitted for clarity.

The gear arrangement 30 is shown in more detail in FIGS. 3 and 4, and comprises a mean gear wheel 40 rotatably mounted at one side of the neck portion 21. The gear arrangement 30 further includes two pairs of roller drive members 42, 44. The roller drive members 42, 44 of each pair are arranged in an opposed relationship relative to each other to define therebetween a path 46, shown in broken lines in FIG. 4. In use, the cleaning member 14 passes along the path 46 in engagement with the roller drive members 42, 44.

As can be seen from FIG. 3, respective further gears 48, 48A, 50 and 50A are provided at one end each of the roller drive members 42, 44. As can be seen from FIG. 4, the gears 48, 50 are mounted on the upper roller members 42, 44, and the further gears 48A, 50A are mounted on the lower roller members 42, 44.

The main gear wheel 40 and the further gears 48, 48A, 50, 50A are provided with teeth to allow meshing engagement therebetween. The gear members 48, 50 are arranged in direct meshing engagement with the main gear wheel 40. The further gear members 48A, 50A on the lower roller members 42, 44 are arranged in indirect meshing engagement with the main gear wheel 40, with a subsidiary gear 53 arranged between the further gears 48A, 50A and the main gear wheel 40.

Thus, rotation of the main gear wheel 40 by means which is described below, in the direction of the arrow X drives the further gears 48, 48A 50, 50A in the directions indicated by the arrows Y and Z.

In view of the fact that the roller drive members 42, 44 are fixedly mounted on the respective further gears 48, 48A, 50, 50A, rotation of the further gears 48, 48A, 50, 50A in the directions indicated by the arrows Y and Z means that the roller members 42, 44 are also rotated in the directions indicated by the arrows Y and Z. This has the effect of driving the cleaning member 14 through the feeder 20 in the direction indicated by the arrow F. It will be appreciated that, if the main gear wheel 40 is driven in the direction opposite to the arrow X, then the elongate cleaning member will be driven in the direction opposite to the arrow F.

The main gear wheel 40 defines a drive aperture 51, having formations in the form of grooves 51A to cooperate with splines on a shaft of a driver, as explained below. The neck portion 21 has a feed aperture 21A (see FIG. 3) aligned with the drive aperture 51.

Figure 5:
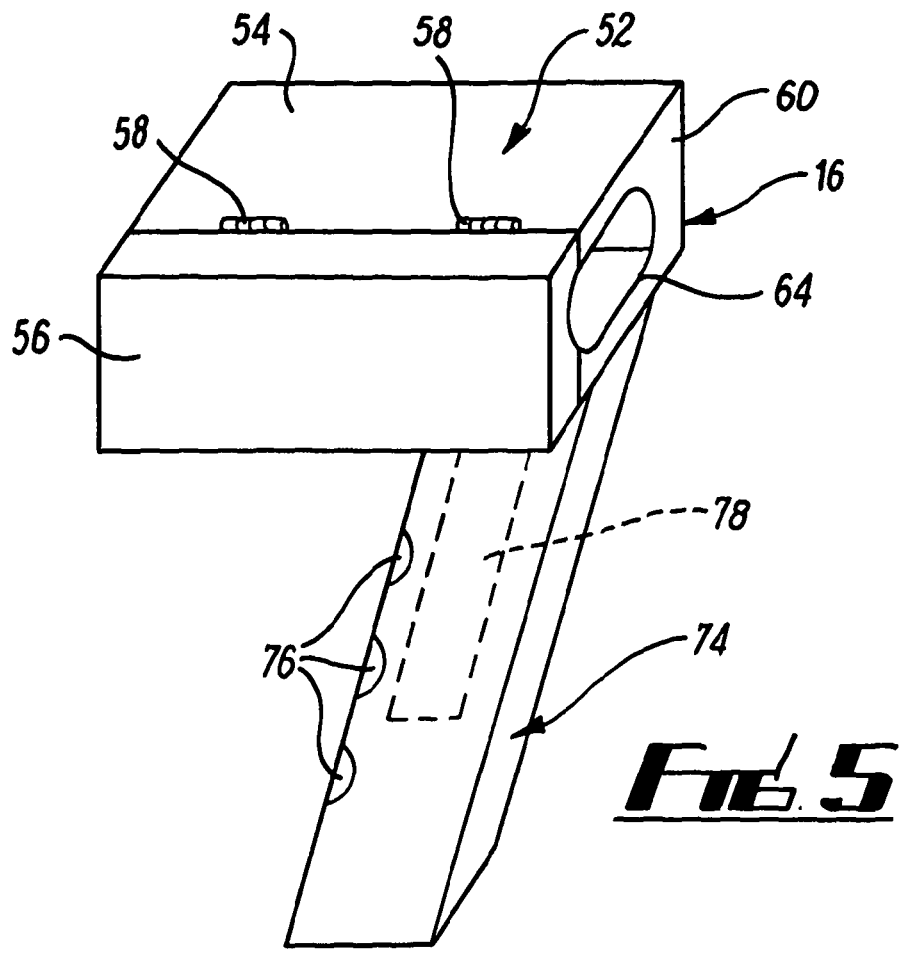
FIG. 5 is a side perspective view of a drive arrangement for use in the cleaning apparatus shown in FIG. 1.

Referring to FIG. 5, there is shown the drive arrangement 16, which comprises a receiving portion 52, for receiving the transmission arrangement 20 of the cartridge 12. The receiving portion 52 comprises a main part 54, and a door 56 which can be opened to allow the tubular member 23 of the cartridge 12 to be inserted into the receiving portion 52. The door 56 can then be closed, and fastened in its closed position, thereby securing the cartridge 12 to the drive arrangement 16. Thus, the receiving portion 52 can hold the cartridge 12. As can be seen from FIG. 5, the door 56 is mounted on the main part 54 by hinges 58.

The receiving portion 52 has opposite ends 60, 62, each defining an aperture 64, through which the tubular member 23 and the locating portion 32 can extend, as shown in FIG. 1.

Figure 6:
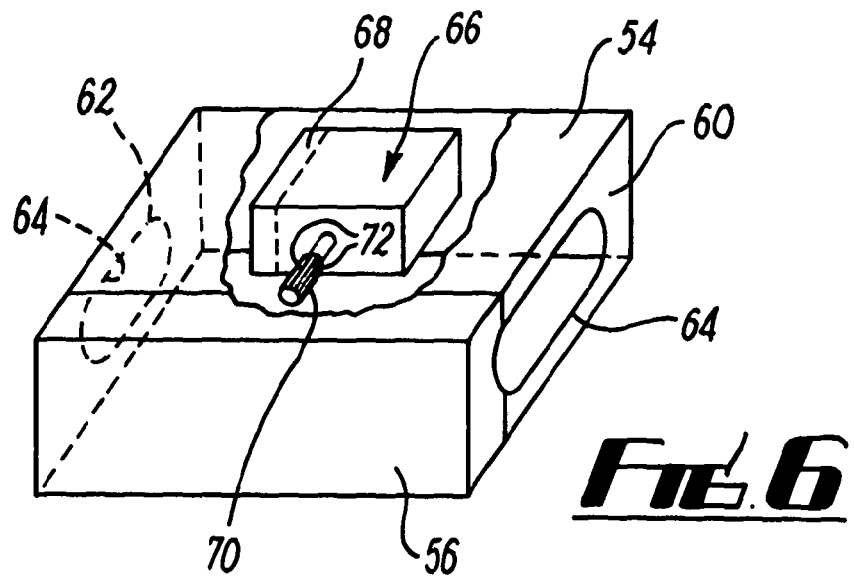
FIG. 6 is a view of a receiving portion of the drive arrangement shown in FIG. 5 with a part cut away so the inside can be seen.

Referring to FIG. 6, there is shown the receiving portion 52, in which a part of the main portion 54 has been cut away, so that the internal region of the receiving portion 52 can be seen.

The main part 54 of the receiving portion 52 houses a driver in the form of a motor 66. The motor 66 is controlled by a controller, which in the embodiment shown, is a micro-processor 68.

A drive member in the form of a shaft 70 extends from the motor 66. The shaft 70 is provided with co-operating formations in the form of splines 72 which co-operate with the grooves 51A defined at the drive aperture 51 in the main gear wheel 40 of the cartridge 12.

In order to mount the cartridge 12 on the drive arrangement 16, the door 56 is opened, and the transmission arrangement 20 inserted therein such that the aperture 21A in the neck portion 21 and the aperture 51 in the main gear wheel 40 receive the shaft 70. The splines 72 on the shaft 70 co-operatively engage the grooves 51A at the aperture 51 in the main gear wheel 40.

With the shaft 70 cooperatively engaged in the driving aperture 51 in the main gear wheel 40, the shaft 70 can be driven about its longitudinal axis, so that torque is transmitted to the main gear wheel 40. The torque is, in turn, is transmitted by the main gear wheel 40 via the further gears 48, 48A, 50 and 50A to the roller drive member 42, 44 to drive the flexible cleaning member 14.

The drive arrangement 16 further includes a handle 74 by which the drive arrangement 16 can be held by a user. Control members in the form of buttons 76 are provided on the handle 74. The handle 74 extends downwardly from the receiving portion 52.

Batteries 78, shown in broken lines in FIGS. 1 and 5 may be mounted within the handle 74 to provide power to the motor 66.

In the embodiment described herein, the micro-processor 68 is configured, or programmed, to allow the user to select how the elongate member 14 is driven. In particular, the micro-processor 68 is programmed to allow the elongate member to be driven forwards out of the locating portion 34 or, in the reverse direction, back into the locating portion 34. Alternatively, if more thorough cleaning is required, the microprocessor is programmed to allow oscillatory, or reciprocating, of the elongate member 14.

There is thus described a cleaning apparatus, a cleaning member, a holding arrangement for the cleaning member, and a drive arrangement for driving the cleaning member which enable the internal regions of an article, such as an endoscope to be cleaned efficiently and easily.

Various modifications can be made without departing from the scope of the invention. For example, the shape of the receiving portion 52 and/or the handle 74 could be of any suitable other shape. Also the driver can be any suitable type of motor, and the configuration and/or alignment thereof can be different to that shown in the drawings. The cleaning member 14 may have any other suitable number of brush portions 14B, such as two or four.

It is also envisaged that the gear arrangement can be different to that shown in the drawings, the precise arrangement of the gears being determined by the purpose of driving the cleaning member.

Figure 9:
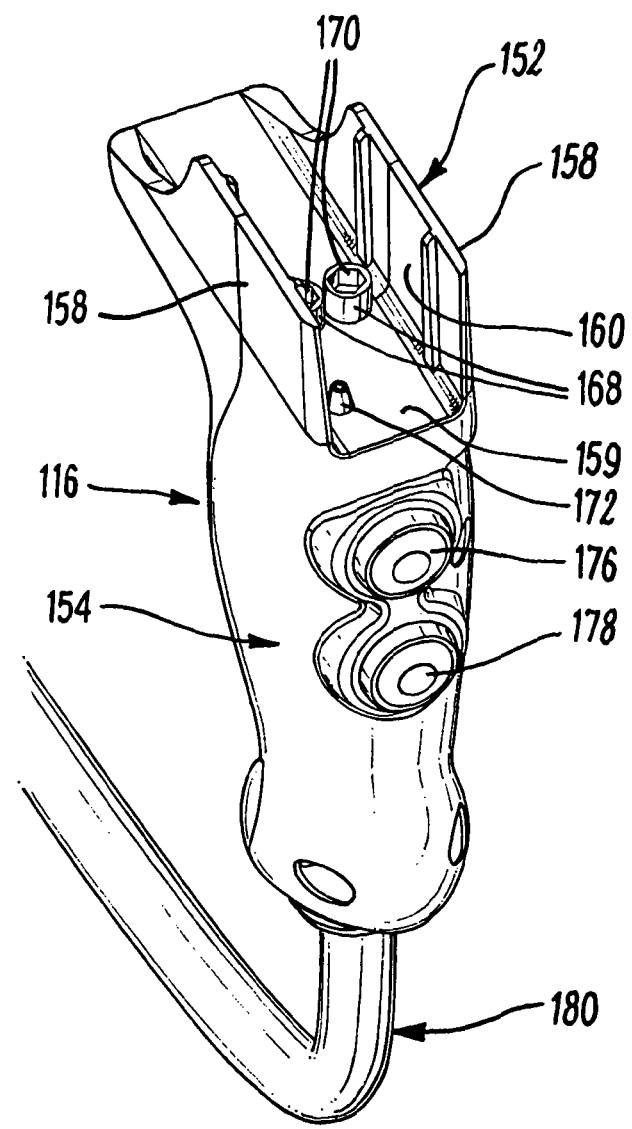
FIG. 9 shows a perspective view of the cleaning apparatus shown in FIGS. 7 and 8.
Figure 10:
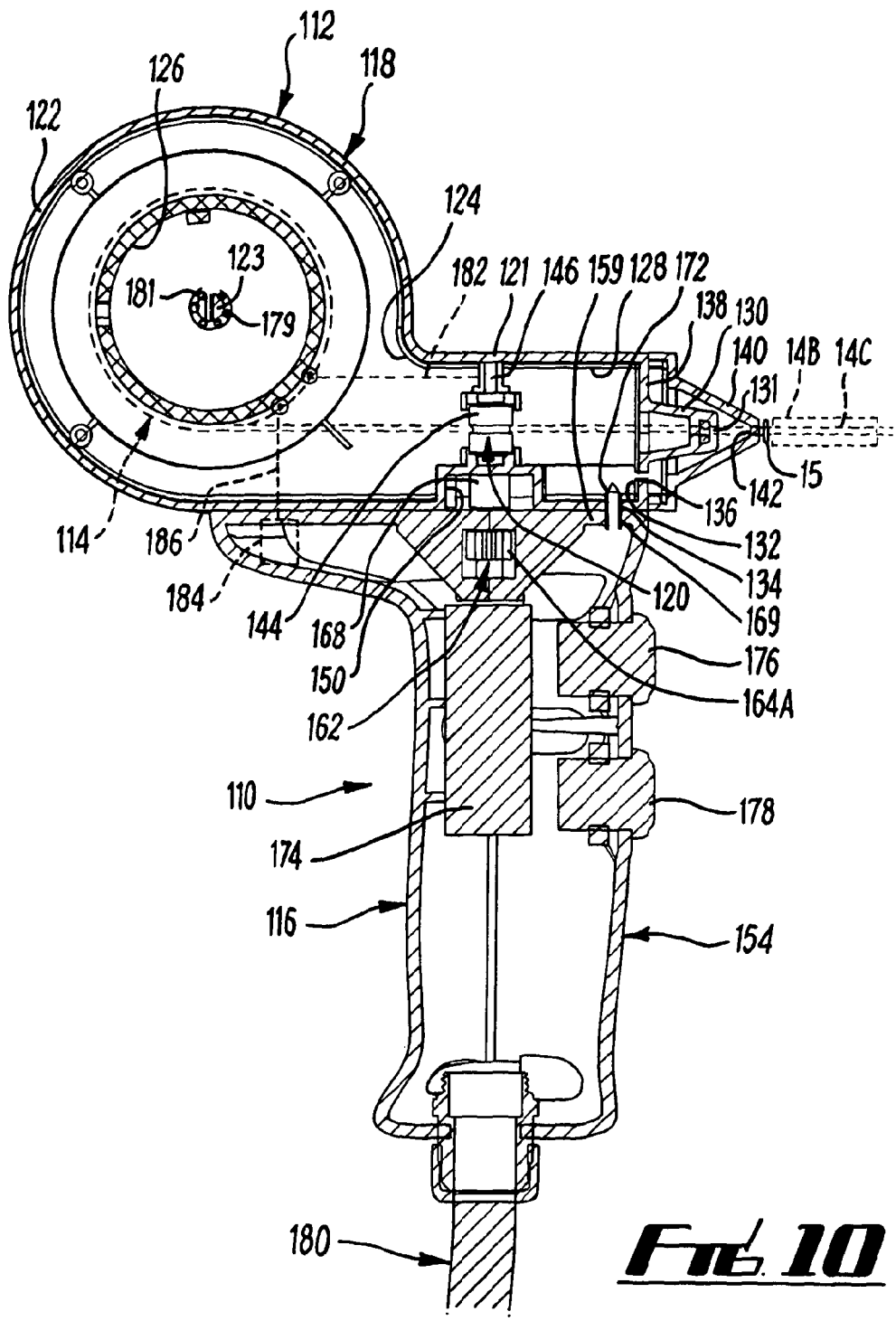
FIG. 10 shows a side sectional view of the cleaning apparatus shown in FIGS. 7 and 8.

A further embodiment is shown in FIGS. 7 to 11, in which a cleaning apparatus 110 comprises a holding arrangement in the form of a cartridge 112 for holding a flexible elongate cleaning member 114 (shown in broken lines in FIG. 10). As shown, the cleaning apparatus 110 further includes a hand-held drive arrangement 116, upon which the cartridge 112 can be mounted.

The flexible elongate cleaning member 114 is the same as the flexible elongate cleaning member 14 described above, and comprises an elongate flexible shaft 14A, three brush portions 14B at the distal end region 14C of the shaft 14A, and a stopper 15 on the shaft 14A spaced towards the proximal end region from all three brush portions 14B. The cartridge 112 comprises a housing 118 and a transmission arrangement 120, which is shown in more detail in FIGS. 10 and 11.

Referring to FIG. 10, the cartridge 112 comprises a main portion in the form of a mounting element 122 which houses a holding element in the form of a reel 126 upon which the flexible elongate cleaning member 114 is wound. The reel 126 is rotatably mounted on the mounting element 122 at a spindle 123.

The mounting element 122 is of a generally cylindrical configuration and defines an opening 124. The housing 18 further includes a neck portion 121 defining a channel 128 which communicates with the mounting element 122 via the opening 124. The neck portion 121 may constitute a neck of the cartridge 112.

An end wall 138 is provided at the opposite end of the neck portion 121 to the opening 124. The end wall 138 has first a feed nozzle 130 thereon. The first feed nozzle 130 defines an aperture 131.

The neck portion 121 defines a chamber 132 at a lower region thereof. The chamber 132 can receive cleaning fluid from a pipe (not shown in the drawings). An inlet aperture 134 is defined in a lower wall of the chamber 132 to allow cleaning fluid to be supplied to the chamber 132. An outlet aperture 136 is defined in the end wall 138 of the neck portion 121. The inlet aperture 134 receives therethrough a fluid supply nozzle 172 on the drive arrangement 116, as explained below.

An outer nozzle 140 defining an aperture 142 is provided around the inner nozzle 130, and cleaning fluid from the chamber 132 is supplied via the outer aperture 136 into the space between the outer nozzle 140 and the inner nozzle 130. The cleaning fluid is supplied to the article to be cleaned with the elongate cleaning member 114 via the aperture 142 in the outer nozzle 140.

Figure 7:
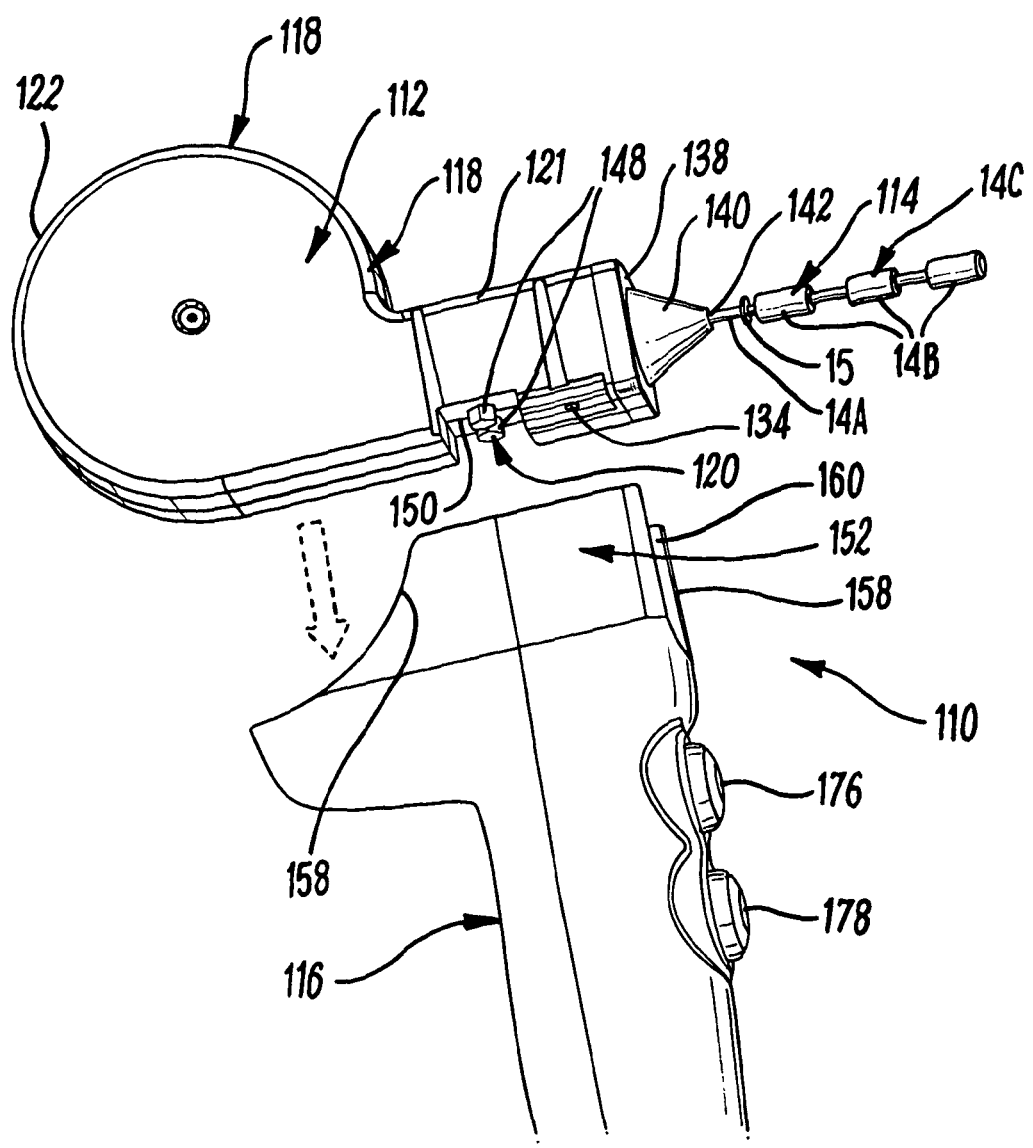
FIG. 7 shows a further embodiment of the cleaning apparatus, with a holding arrangement being mounted on a drive arrangement.
Figure 8:
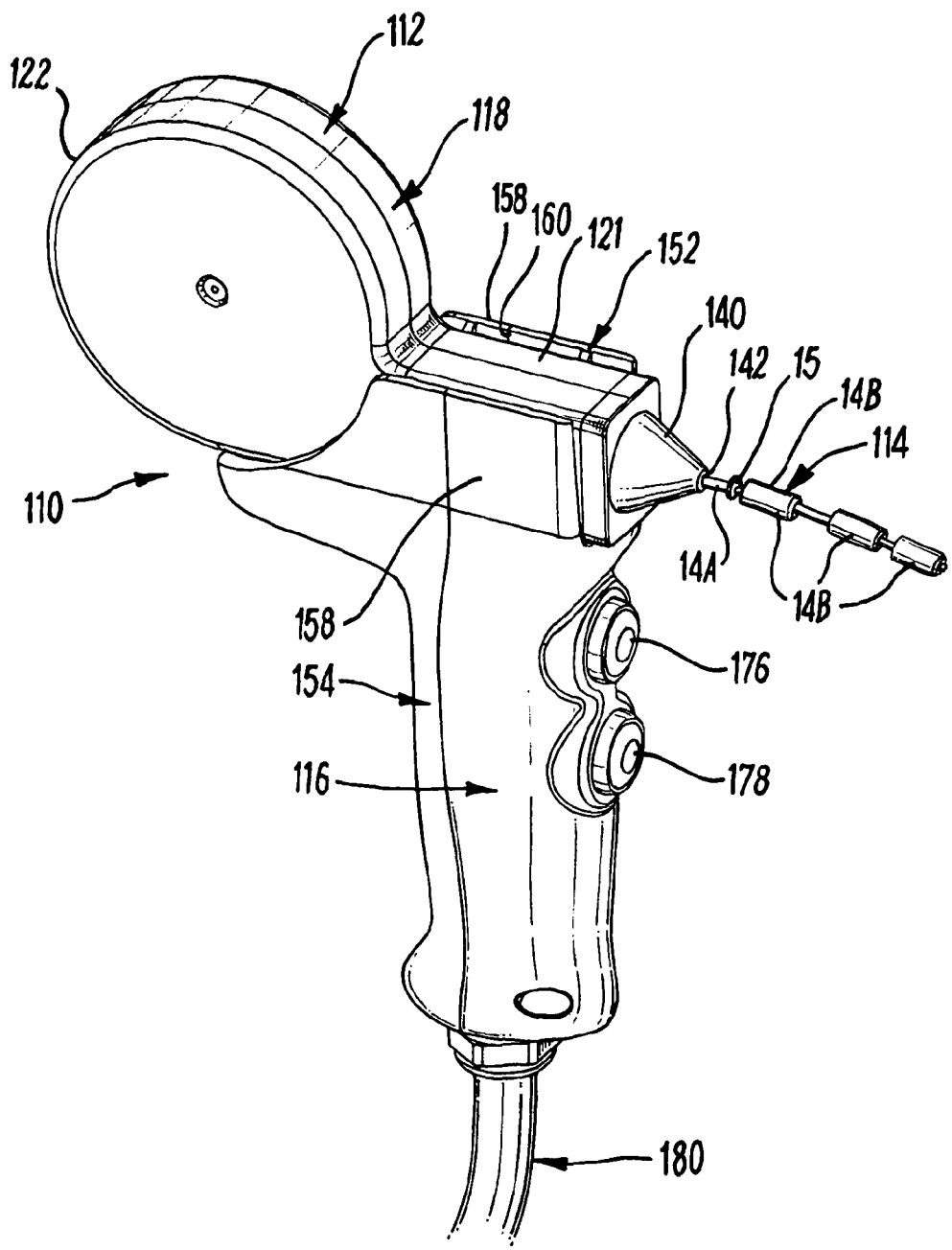
FIG. 8 shows the cleaning apparatus shown in FIG. 7, with the holding arrangement on the drive arrangement.

The transmission arrangement 120 comprises a pair of roller members 144, which are mounted on respective shafts 146. The shafts 146 extend downwardly through the roller members 144 to a region external of the neck portion 121 and terminate in a hexagonal propelled member 148, as shown in FIGS. 7 and 11. As can be seen from FIG. 7, the propelled members 148 are provided within a recess 150 defined in the neck portion 121. The function of the propelled members is described below.

As shown best in FIG. 9, the drive arrangement 116 comprises a receiving portion 152 and a handle 154. The receiving portion 152 comprises a pair of opposed side wall members 158 and a base wall member 159. A holding recess 160 is defined between the side wall members 158. The handle 154 allows the cleaning apparatus 110 to be held in a user's hand.

The neck portion 121 of the cartridge 112 is received in the holding recess 160. This is shown most clearly in FIG. 8.

Referring to FIGS. 9 and 10, the drive arrangement 116 comprises a gear arrangement 162 mounted within the handle 154. The gear arrangement 162 comprises first and second gear wheels 164A, 164B, in meshing engagement with each other.

A shaft 166 is fixedly mounted on each of the gear wheels 164, and extends upwardly therefrom to a respective propelling member 168. Each propelling member 168 defines a hexagonal recess 170 in which a respective one of the hexagonal members 148 can be received.

A fluid supply aperture 169 is defined in the base wall member 159. The fluid supply nozzle 172 is mounted in, and extends through, the fluid supply aperture 169. When the neck portion 121 is received in the holding recess 160, the inlet aperture 134 is aligned with the fluid supply aperture 169, and the fluid supply nozzle 172 is received through the inlet aperture 134. The fluid supply nozzle 172 is connected to a suitable fluid supply pipe (not shown). Thus, cleaning fluid is supplied via the fluid supply nozzle 172, which is received in the fluid supply aperture 169 and the inlet aperture 134.

The first gear wheels 164A is connected to a driver in the form of an electric motor 174, which is operated by forward and reverse buttons 176, 178. The operation of the electric motor 174 is explained below. The second gear wheel 164B is arranged in meshing engagement with the first gear wheel 164A, and is driven by the first gear wheel 164A when the electric motor 174 is operated.

Supply means in the form of a flexible hose 180 is provided to supply electricity and cleaning fluid to the cleaning arrangement 110. The flexible hose 180 carries electric cables which are connected to the electric motor 174 and to the forward and reverse buttons 176, 178. The flexible hose 180 also carries a fluid supply pipe which is connected in fluid communication with the fluid supply nozzle 172. The electric cables and the fluid supply pipe are not shown for reasons of clarity in the drawings.

The fluid supply pipe is connected via a pump (not shown) to a supply of cleaning fluid (also not shown). The electric cables are connected to a control arrangement, comprising appropriate electrical circuitry as would be understood by those skilled in the art for controlling forward and reverse motion of the electrical motor and, hence, forward and reverse motion of the cleaning member 114, and of the reel 126.

The control unit may be suitably programmed to effect progressive reciprocal motion of the electric motor, and hence the cleaning member 114 during cleaning. Thus, during feeding and retraction of the cleaning member 114, the cleaning member 114 may move forwards and backwards. For example, when the forward button 176 is depressed to feed the cleaning member 114, the control unit may effect forward motion of the electrical motor for 2 seconds, and reverse motion for 1 second. This cycle of forward motion for 2 seconds and reverse motion for 1 second would be repeated while the forward button 176 is depressed.

The control unit may be programmed to effect similar motion during depression of the reverse button 178 to retract the cleaning member 114. For example, when the reverse button 178 is depressed, the control unit may effect reverse motion for a period of 2 seconds followed by forward motion of 1 second. This forward and reverse motion would be repeated while the reverse button 178 is depressed. In order to facilitate the reverse motion of the reel 126, urging means in the form of a spring 179 may be provided. Alternatively, or in addition, to the spring 179, bearings 181 may be provided between the spindle 123 and the reel 126.

In a further embodiment, the reel 126 may be driven in the forward and reverse directions directly by a linkage in the form of either a torque transmission rod 182 or a combination of a second motor 184 and a torque transmission rod 186.

Where the linkage comprises the torque transmission rod 182, the torque transmission rod 182 is mounted in the cartridge 112, and is drivingly connected at one end thereof to the shaft 146, and at the opposite end to the reel 126. Operation of the motor 174 in either the forwards or reverse directions causes rotation of the shaft 146 which, in turn drives the reel 126 via the torque transmission rod 182 in the forward or reverse directions.

Where the linkage comprises the second motor 184 and the torque transmission rod 186, the second motor 184 is mounted in the handle 154, and the torque transmission rod 186 extends from the second motor out of the handle 154 to be received in the cartridge 112, when the cartridge 112 is received in the holding recess 160, the torque transmission rod 186 drivingly engages the reel 126.

Operation of the second motor 184 rotates the torque transmission rod 186 and drives the reel 126 in the forward or reverse directions. The second motor 184 is electrically connected to the forward and reverse buttons 176, 178, so that depression of either of the forward and reverse buttons operates the motor 174 and the second motor 184.

It will be appreciated by those skilled in the art that the selection of appropriate time periods for the forward and reverse motion of the electric motor 174 during depression of the forward or reverse buttons can be any suitable time limit to effect suitable cleaning of the article.

As can be seen from FIG. 10, the elongate cleaning member 114 protrudes out of the second nozzle 140. This provides an advantage that it allows the operator to feed the cleaning member 114 into the appropriate channel in the article (for example an endoscope) to be cleaned. A failure to direct the cleaning member into the appropriate channel can result in the cleaning member being delivered to the same channel each time it is cleaned thereby only cleaning one of the channels and failing to clean the others.

In operation, the user mounts a clean cartridge 112 on the drive arrangement 116, and then presents the protruding part of the cleaning member 114 to the endoscope to be cleaned. The user then manually feeds the protruding part of the elongate cleaning member 114 into the channel which the user wishes to clean, and when received therein, the user presses the forward button 176 to feed the cleaning member 114. The control unit operates the motor to effect progressive forward reciprocating motion, for example driving the flexible cleaning element forward for 2 seconds then reversing it for 1 second and continually repeating this cycle until the end of the elongate cleaning member has passed all the way through the channel being cleaned.

As soon as the user is satisfied that appropriate cleaning of the channel has been effected, the user then presses the reverse button 178 to retract the cleaning member. The control unit operates the electric motor in a way that effects reverse progressive reciprocal motion of the flexible elongate member for example by reversing the flexible elongate member for 2 seconds and driving it forward for 1 second. This reverse reciprocal motion is repeated until the flexible elongate member is fully withdrawn from the channel being cleaned. After the channel has been cleaned, and the cleaning member retracted, the used cartridge 112 is then disposed of.

In order to clean another of the channels, a further cartridge 112 is selected by the user and the above process is repeated with the user initially directing the protruding part of the flexible elongate cleaning member into the second channel to be cleaned. The above process can be repeated for all channels.

Figure 12:
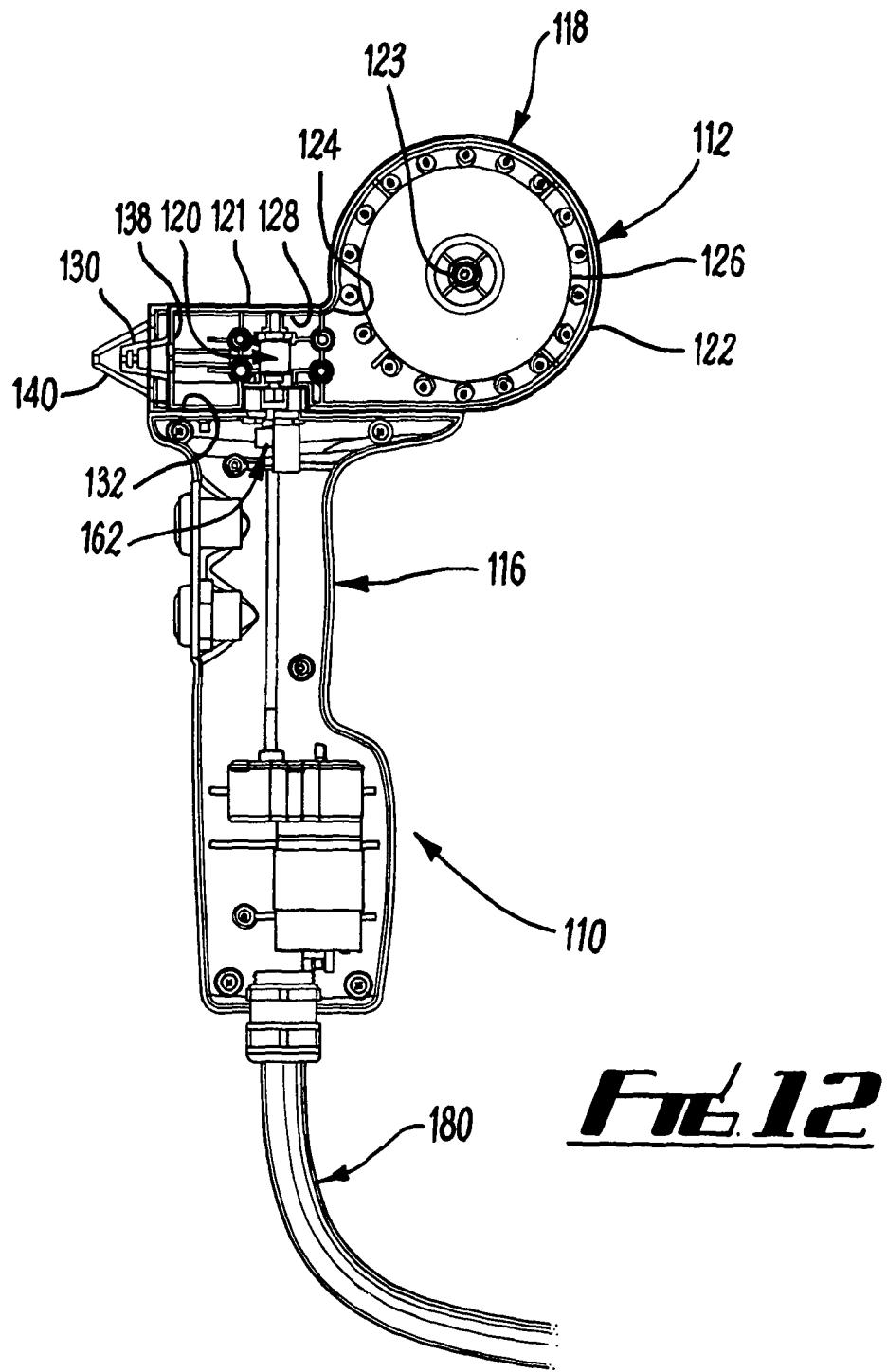
FIG. 12 shows a further embodiment of a cleaning apparatus.
Figure 13:
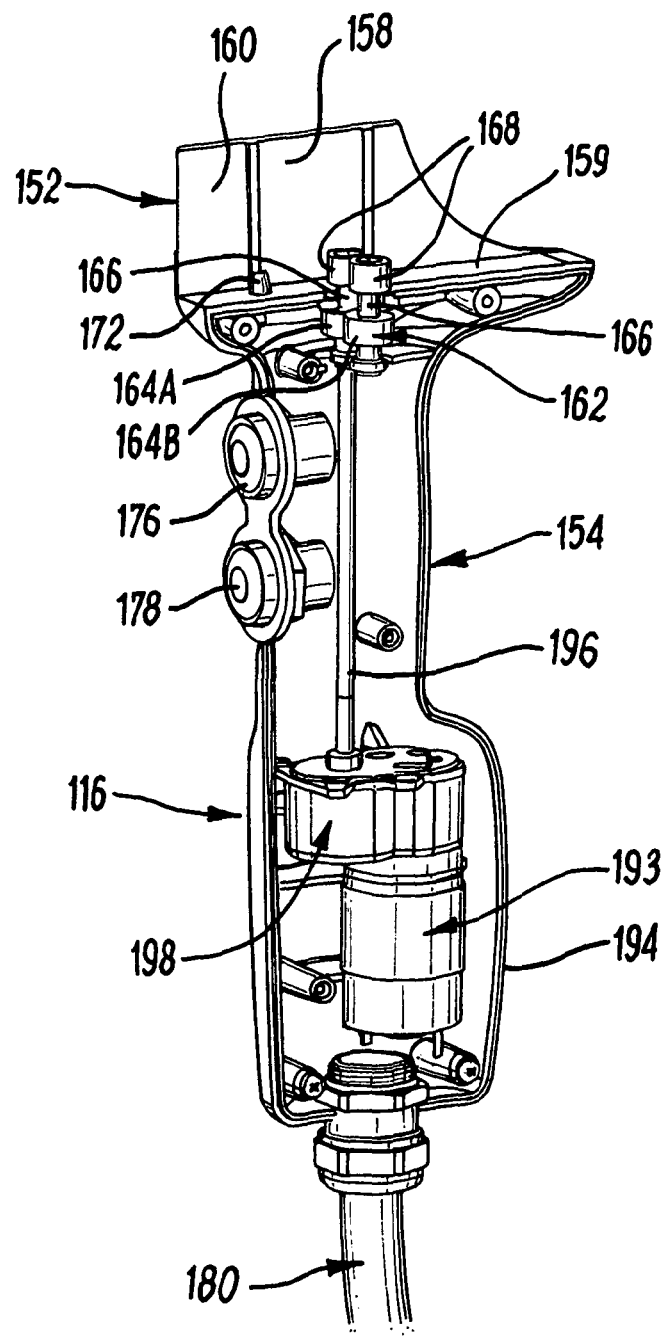
FIG. 13 shows a further embodiment of a drive arrangement for use in the cleaning apparatus shown in FIG. 12.
Figure 14:
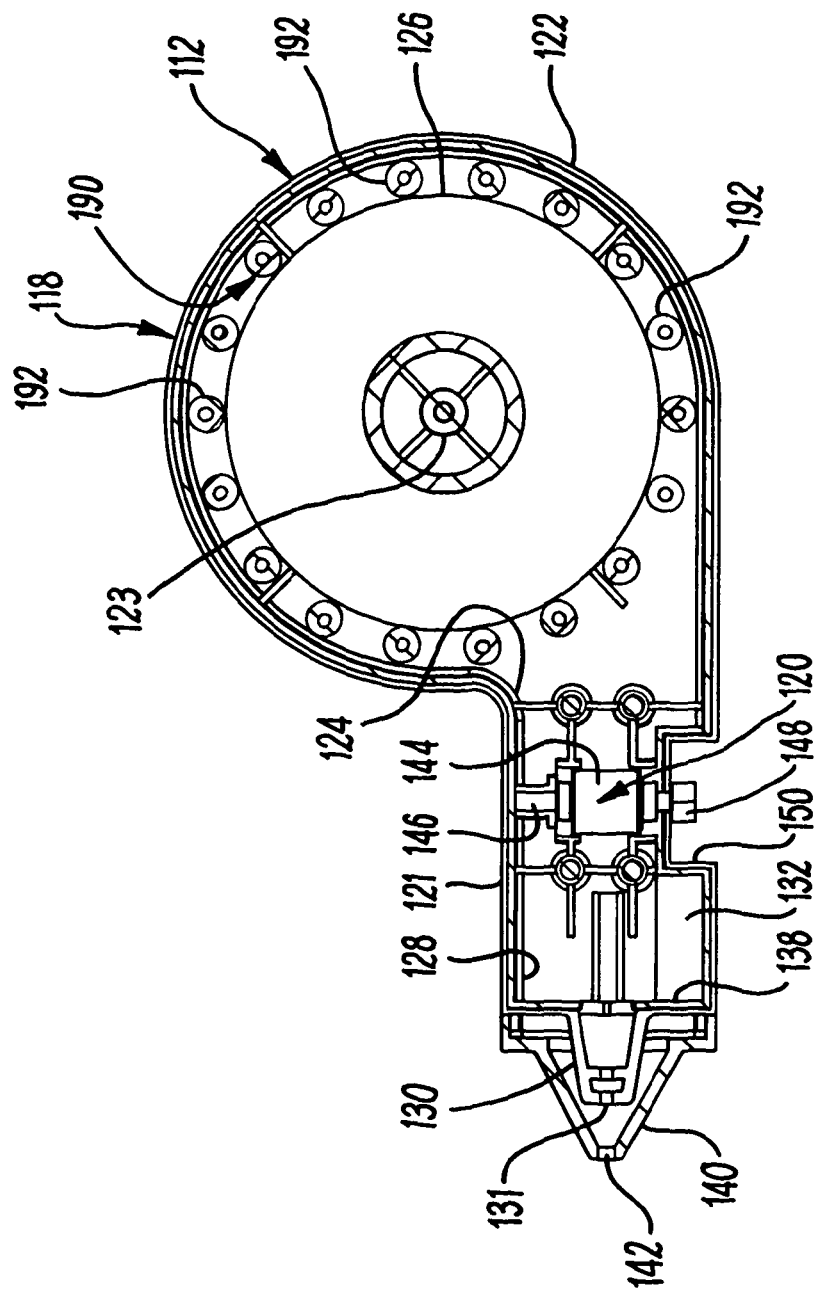
FIG. 14 shows a further embodiment of a holding arrangement for use in the cleaning apparatus shown in FIG. 12.

FIGS. 12 to 14 show a further embodiment of the cleaning apparatus 110, which comprises many of the features of the cleaning apparatus 110 shown in FIGS. 7 to 11, and those features have been designated with the same reference numerals as the corresponding features in FIGS. 7 to 11.

The cleaning apparatus 110 shown in FIGS. 12 to 14 differs from the embodiment shown in FIGS. 7 to 11 in that the holding arrangement 118 comprises a friction reducing means in the form of a guide arrangement 190, which comprises a plurality of rollers 192 arranged around the periphery of the reel 126. The rollers 192 guide the elongate cleaning member 114 onto the reel 126 during retraction of the elongate cleaning member 114. The rollers 192 act as the friction reducing means by reducing friction between the mounting element 122 and the elongate cleaning member 114. Without the guide arrangement 190, the cleaning member 114 can engage the mounting element 122 during retraction, which can prevent the elongate cleaning member 114 from being rewound onto the reel 126. In the embodiment shown, the rollers 192 prevent engagement of the cleaning member 114 with the mounting element 122 and allow unrestricted movement of the elongate cleaning member 114 during retraction thereof.

Figure 15:
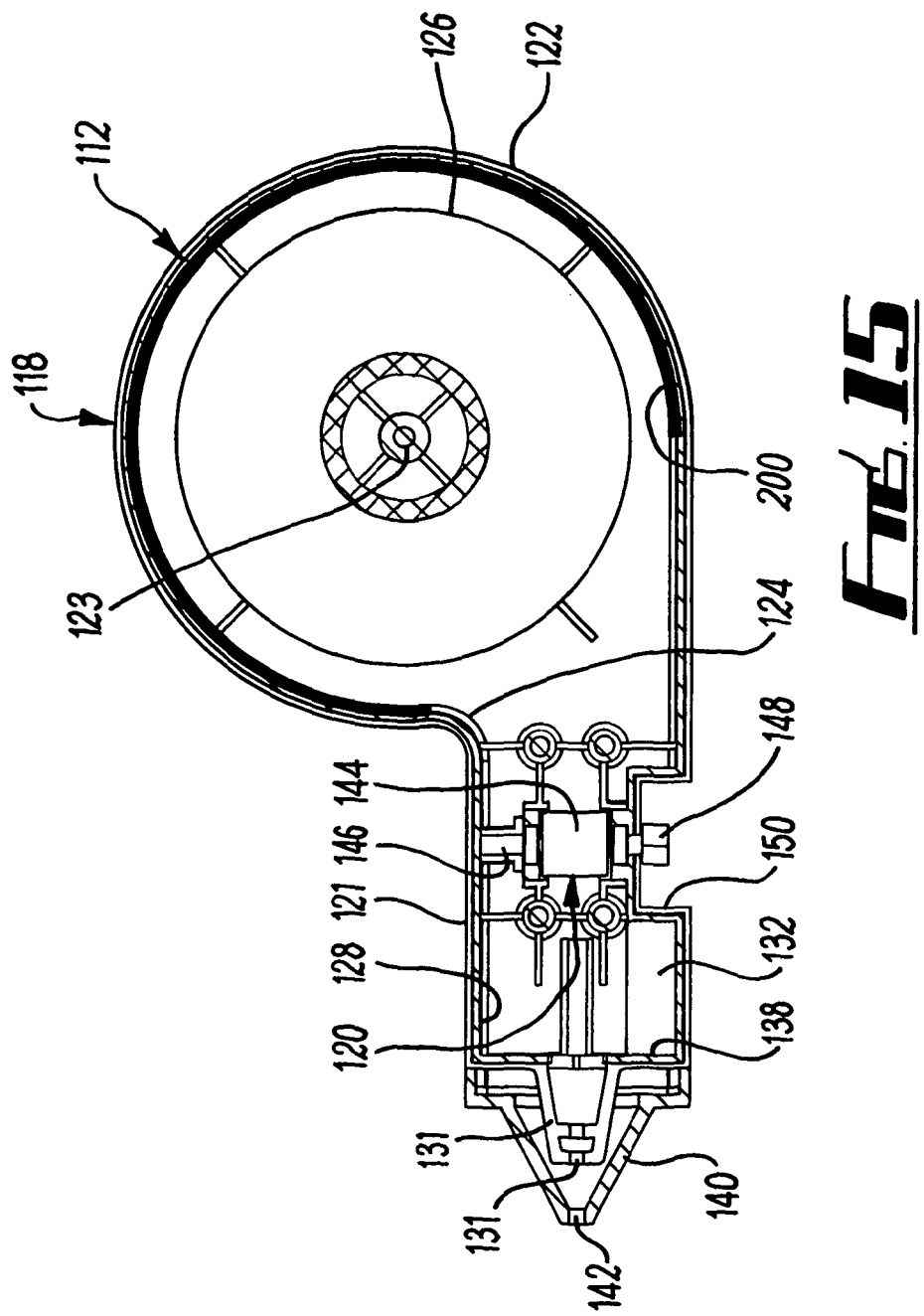
FIG. 15 shows another embodiment of a holding arrangement for use with the cleaning apparatus shown in FIG. 12.

Referring to FIG. 15, a further embodiment of the holding arrangement 116 is shown, in which the friction reducing means comprises a strip 200 of a low friction material extending around the inner surface of the mounting element 122. A suitable low friction material is PTFE.

A further modification is shown in FIGS. 12 to 14 is that an electric motor 193 is disposed at the proximal end 194 of the handle 154. The electric motor 193 replaces the electric motor 174. As can be seen from FIGS. 12 and 13, the handle 154 is wider at the proximal end 194 than the embodiment shown in FIGS. 7 to 11. This is to accommodate the electric motor 193.

A drive shaft 196 extends from a gear mounting 198 to the first gear wheel 164A. The gear mounting 198 is provided on the electric motor 193 and transmits drive from the electric motor 193 to the shaft 196, which in turn transmits the drive to the first gear wheel 164A. The second gear wheel 164B is driven by the first gear wheel 164A in the same way as described above.

The invention claimed is:

1. A cleaning apparatus comprising a drive arrangement and a cartridge removably mountable on the drive arrangement, wherein the cartridge comprises:
    a flexible elongate cleaning member;
    a housing for housing at least a portion of the flexible elongate cleaning member;
    a holding element within said housing for holding the flexible elongate cleaning member; and
    a transmission arrangement within said housing, said transmission arrangement being separate from the holding element to transmit drive from the drive arrangement to the flexible elongate cleaning member to drive the cleaning member lengthwise; and
    wherein the drive arrangement comprises a handle to facilitate the drive arrangement being held by a user.

2. A cleaning apparatus according to claim 1, wherein the holding element comprises a reel rotatably mounted on said housing, the cleaning member being wound on the reel, and wherein the reel is rotatable in a first direction to feed the elongate cleaning member from the holding arrangement, and in a second direction opposite to the first direction to retract the elongate cleaning member into the holding arrangement.

3. A cleaning apparatus according to claim 2, including impelling means to impel the holding element in the second direction, wherein the impelling means comprises a linkage which extends from the transmission arrangement to the holding arrangement.

4. A cleaning apparatus according to claim 2, including impelling means to impel the holding element in the second direction, wherein the impelling means comprises a second drive arrangement configured to drive the holding arrangement, and a linkage extending from the second drive arrangement to the holding arrangement.

5. A cleaning apparatus according to claim 1, wherein the cartridge comprises a main portion in which the holding element is housed, and a neck portion extending forwardly of the main portion.

6. A cleaning apparatus according to claim 5, wherein the cartridge comprises a locating portion for locating the cartridge at an appropriate position on the article to be cleaned, the locating portion being configured for directing the cleaning member into an appropriate region of the article to be cleaned.

7. A cleaning apparatus according to claim 6, wherein the cleaning member protrudes from the locating portion prior to use.

8. A cleaning apparatus according to claim 6, wherein the locating portion defines a directing conduit, which extends through the locating portion, and wherein a fluid supply conduit is defined on the locating portion to supply cleaning fluid to the cleaning member to facilitate cleaning of the article, the fluid supply conduit being in fluid communication with the directing conduit.

9. A cleaning apparatus according to claim 1, wherein the transmission arrangement comprises at least one pair of roller drive members, said roller drive members defining a feed path through which the cleaning member can extend, the roller drive members being positioned to engage the cleaning member in the feed path.

10. A cleaning apparatus according to claim 1, wherein the transmission arrangement comprises propelled members arranged to co-operate with propelling members on the drive arrangement.

11. A cleaning apparatus according to claim 10, wherein the propelled members are attached to the roller drive members.

12. A cleaning apparatus according to claim 1, wherein the drive arrangement includes a receiving portion in which at least a part of the cartridge can extend, and the drive arrangement further includes a driver for driving the flexible elongate cleaning member.

13. A cleaning apparatus according to claim 12, wherein the receiving portion comprises a pair of opposed side wall members, and a neck portion of the cartridge can be received between the wall members.

14. A cartridge removably mountable on a drive arrangement to provide a cleaning apparatus, the cartridge comprising: a flexible elongate cleaning member; a housing for housing at least a portion of the flexible elongate cleaning member; a holding element within said housing for holding the flexible elongate cleaning member, the holding element being rotatably mounted on the housing; a transmission arrangement within said housing, said transmission arrangement comprising at least one pair of roller drive members to transmit drive from the drive arrangement to the flexible elongate cleaning member wherein the drive arrangement comprises a handle to facilitate the drive arrangement being held by a user.

15. A cartridge according to claim 14, wherein the holding element comprises a reel, and the cleaning member is wound on the reel, and wherein the holding element is rotatable in a first direction to feed the elongate cleaning member from the holding arrangement, and in a second direction opposite to the first direction to retract the elongate cleaning member into the holding arrangement.

16. A cartridge according to claim 14, comprising a main portion in which the holding element is housed, a neck portion extending forwardly of the main portion, and a locating portion for locating the cartridge at an appropriate position on the article to be cleaned, the locating portion being configured for directing the cleaning member into an appropriate region of the article to be cleaned.

17. A cartridge according to claim 16, wherein the cleaning member protrudes from the locating portion prior to use.

18. A cartridge according to claim 16, wherein a fluid supply conduit is defined on the locating portion to supply cleaning fluid to the cleaning member to facilitate cleaning of the article, the fluid supply conduit being in fluid communication with the directing conduit.

19. A cartridge according to claim 14, wherein the transmission arrangement comprises at least one pair of roller drive member for engaging the cleaning member, and wherein a feed path is defined by the roller drive members through which the cleaning member can extend, the roller drive members being positioned to engage the cleaning member in the feed path.

20. A cartridge according to claim 14, wherein the transmission arrangement comprises propelled members arranged to co-operate with propelling members on the drive arrangement, the propelled members being attached to the roller drive members.

* * * * *